United States Patent [19]

Hoch et al.

[11] 4,252,748

[45] Feb. 24, 1981

[54] RECOVERY OF ACETONE PRODUCED BY CARBONYLATION

[75] Inventors: Robert Hoch; James Leacock, both of New York, N.Y.; Chee-Gen Wan, North Brunswick, N.J.

[73] Assignee: Halcon Research and Development Corporation, New York, N.Y.

[21] Appl. No.: 974,291

[22] Filed: Dec. 29, 1978

[51] Int. Cl.³ .............................................. C07C 45/80
[52] U.S. Cl. .................................. 568/411; 568/387; 203/62; 203/60
[58] Field of Search ................ 260/593 P; 203/62, 65, 203/67, 75, 60

[56] References Cited

U.S. PATENT DOCUMENTS

| | | | |
|---|---|---|---|
| 2,212,810 | 8/1940 | Field | 260/593 P |
| 2,604,439 | 7/1952 | Nixon | 203/62 |
| 2,704,271 | 3/1955 | Harrison et al. | 203/75 |
| 3,182,006 | 5/1965 | Fruhwirth | 203/67 |
| 3,288,877 | 11/1966 | Taylor et al. | 203/62 |
| 3,419,477 | 12/1968 | Mattia | 203/67 |
| 3,433,831 | 3/1969 | Yomiyama et al. | 203/62 |
| 4,153,516 | 5/1979 | Reed et al. | 203/63 |
| 4,163,696 | 8/1979 | Wong | 260/593 P |

OTHER PUBLICATIONS

Lecat, Ann Chem., vol. 12(2), pp. 158–202.

*Primary Examiner*—James H. Reamer
*Attorney, Agent, or Firm*—William C. Long; David Dick; Riggs T. Stewart

[57] ABSTRACT

Acetone produced as a by-product in the reaction of methyl acetate with carbon monoxide and hydrogen in the presence of a Group VIII noble metal catalyst and methyl iodide is recovered from the reaction mixture by supplying acetone to provide an acetone to methyl iodide molar ratio of at least 1:10 and distilling the mixture comprising methyl iodide, acetone and methyl acetate to separate substantially all of the methyl iodide and the supplied acetone and some of the methyl acetate from the remaining acetone and methyl acetate and thereafter separating the acetone from the methyl acetate.

4 Claims, 1 Drawing Figure

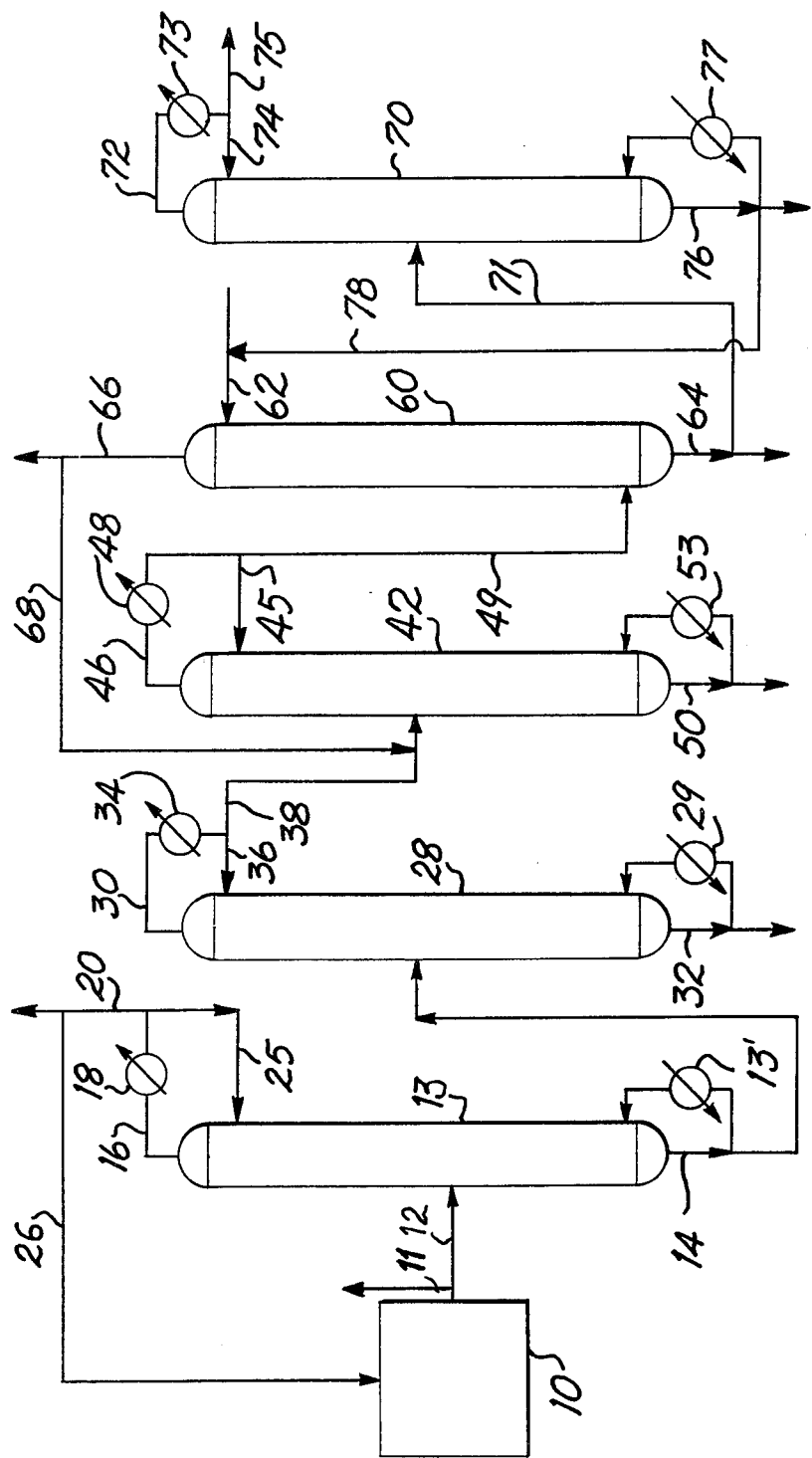

RECOVERY OF ACETONE PRODUCED BY CARBONYLATION

This invention relates to the separation of by-products from the reaction mixture produced in the carbonylation of methyl acetate and is more particularly concerned with the separation of acetone from such a mixture.

The carbonylation of methyl acetate in the presence of carbon monoxide and hydrogen is described in Belgian Pat. No. 839,320 which is a counter-part of co-pending U.S. application Ser. No. 654,662 filed Feb. 5, 1976. Such carbonylation as described in the Belgian patent and in the co-pending application involves the reaction of methyl acetate or dimethyl ether with carbon monoxide and hydrogen in a substantially anhydrous environment in the presence of a Group VIII noble metal catalyst, such as a rhodium or palladium catalyst, and in the presence of an iodide such as methyl iodide, preferably also in the presence of a promoter for the Group VIII noble catalyst. The principal products of this reaction, which will vary in their relative proportions with variations in the catalysts and/or the reaction conditions, ordinarily comprise ethylidene diacetate, acetic anhydride, acetic acid and acetaldehyde. The reaction mixture also contains methyl iodide and unreacted methyl acetate and may contain some vinyl acetate.

In a typical carbonylation of this type, the volatile portion of the reaction mixture which comprises the above-named compounds is separated from the non-volatile components which comprise primarily the Group VIII noble metal catalyst. In this separation some of the less volatile compounds such as acetic acid, acetic anhydride and ethylidene diacetate may tend to remain with the non-volatile components. The volatile portion which is thus obtained is then ordinarily condensed and fractionally distilled to separate it into its various components. It has been found, however, that small amounts of acetone are also formed in the carbonylation, particularly when a palladium catalyst is employed, and, because of boiling point relationships and the formation of azeotropes, attempts to separate and recover the acetone have encountered serious difficulties. For example, methyl iodide, which is always a component of the reaction mixture, has an atmospheric boiling point of 42.5 and it is known to form a minimum-boiling azeotrope with acetone which has an atmospheric boiling point of 42.4° C. (Lecat, Ann. Chim. (12) 2, 158–202). Thus, ordinary, fractional distillation while effective to separate acetaldehyde, vinyl acetate, acetic anhydride, ethylidene diacetate, methyl iodide and methyl acetate from each other, has not been effective to recover acetone for removal from the system. Separation of acetone and methyl acetate is taught in Harrison et al. U.S. Pat. No. 2,704,271 but, because of the presence of methyl iodide, this technique is ineffective when directly applied to the carbonylation reaction produce mixture. Acetone is a valuable by-product and it is important to recover it in relatively pure form.

It is, accordingly, an object of this invention to provide a process for the effective separation of by-product acetone from carbonylation product mixture.

In accordance with this invention, acetone is effectively removed from the carbonylation reaction product mixture and recovered in relatively pure form by an integrated series of distillation steps which at the same time, facilitate maximum recycle to the carbonylation zone of methyl acetate and methyl iodide. The process of this invention involves treating the volatile components of the carbonylation reaction mixture in a specific sequence of steps which result in the effective recovery of the net "make" of acetone free from the other components of the volatile portion of the carbonylation mixture, which it contaminates and which contaminate it when the mixture is subjected to a conventional sequence of fractional distillation steps.

Thus, in accordance with the invention, the acetone concentration of the volatile component portion or mixture is increased, e.g., by supplying acetone to the carbonylation zone so that the acetone concentration of the volatile mixture in relation to the methyl iodide concentration of the mixture is at least 1 mol per 10 mols of methyl iodide, preferably at least 1.5 mol per 10 mols of methyl iodide and thus "fortified" volatile component mixture is then subjected to fractional distillation to remove a distillate composed of acetone, methyl acetate and methyl iodide, the distillation being carried out to remove essentially all of the methyl iodide in the fortified mixture but only some of the methyl acetate and acetone. In a continuous operation, to which the process of the invention is particularly applicable, the increase in the concentration of acetone in the mixture to be separated is suitably effected, at least in part, by recycling the distillate from the above-mentioned fractional distillation to the carbonylation reaction wherein the acetone by-product is being produced. This recycling also returns methyl acetate and methyl iodide to the carbonylation reaction for reuse. Indeed, maximum recycle of methyl iodide to the carbonylation is desired and the process of this invention brings about maximum recycling of methyl iodide. In some cases the volatile component mixture recovered from the carbonylation reactor also contains acetaldehyde. Advantageously, the low boiling acetaldehyde (b.p. 21° C.) is removed by prior distillation to provide a feed material to be treated for acetone removal.

In the course of the fractional distillation in which the distillate comprising methyl iodide, acetone and methyl acetate is removed, there is obtained a first bottoms product containing acetone, methyl acetate and the other components of the feed to the distillation. This first bottoms product is then distilled to remove as distillate the acetone and the methyl acetate, and the acetone and methyl acetate distillate thus obtained is subjected to azeotropic distillation in the presence of an alkane or alkene containing five carbon atoms, which will be referred to as a "C5 hydrocarbon." Especially preferred is pentane. Other suitable azeotropic agents include 1-pentene, 2-pentene, 2-methylbutane, and 3-methylbutene-1. The bottoms from the distillation to remove acetone and methyl acetate prior to the azeotropic distillation comprise the higher boiling components of the original feed and these can be separated from each other, as desired, in an convenient manner, e.g., by ordinary fractional distillation.

As a result of the azeotropic distillation with the C5 hydrocarbon there is obtained an azeotrope of the C5 hydrocarbon and acetone which is removed as distillate, and the bottoms from this distillation contains the methyl acetate free from acetone and suitable for recycle to the carbonylation reactor as feed for further carbonylation, if desired.

The C5 hydrocarbon-acetone azeotrope obtained as distillate in the azeotropic distillation is now treated to separate the acetone from the C5 hydrocarbon, for example, as described in Harrison et al. U.S. Pat. No. 2,704,271. Preferably, the separation is effected by extraction with water, e.g., by counter-current extraction. As a result of this extraction the by-product acetone is dissolved in the water and separated from the C5 hydrocarbon which can be recycled to the azeotropic distillation. The acetone can be recovered from the water solution, if desired, in conventional manner, e.g., by fractional distillation.

It is believed that the invention will be more fully understood by reference to the accompanying drawing which shows, diagrammatically, a typical system for carrying out the process of the invention.

Referring to the drawing, the reference numeral 10 designates a carbonylation reactor wherein methyl acetate and/or dimethyl ether react with carbon monoxide and hydrogen in the presence of a Group VIII noble metal and an iodine moiety comprising methyl iodide to produce a reaction product comprising acetone. The volatile components of the reaction mixture are removed directly from the reactor if in vapor form, or are separated from the nonvolatile components, e.g., catalyst, in a separation zone (not shown), e.g., a flash distillation zone. Any acetaldehyde present is readily removed as seen at 11 since its high volatility makes its separation by fractional distillation readily achieved. The remainder of the volatile mixture containing the acetone, methyl iodide and methyl acetate, along with any higher boiling components present, passes via line 13 to distillation zone 13. In distillation zone 13, which has a reboiler 13' and a bottoms withdrawal line 14, and is operated at a temperature of 40° to 100° C. under a pressure of 13 to 22 psia, the distillate is removed via line 16, condensed at 18 and withdrawn via line 20, with reflux being returned to the distillation via line 25. Line 20 is connected to the reactor by line 26 for recycling the withdrawn distillate.

The bottoms from distillation zone 13 pass via line 14 into distillation zone 28 provided with a reboiler 29, a distillate line 30 and bottoms draw-off line 32. Distillation zone 28 is operated at a temperature of 40° to 130° C. and under a pressure of 9 to 19 psia. The distillate comprising the acetone-methyl acetate mixture is withdrawn through line 30, condensed at 34 and removed through line 38, with reflux being returned to the distillation column via line 36. The bottoms from distillation zone 28 are withdrawn via line 32 and separated as desired by further distillation (not shown). The acetone-methyl acetate distillate mixture in line 38 is directed into azeotropic distillation zone 42 in which the C5 hydrocarbon azeotropic agent is present. As a result of the azeotropic distillation, a distillate comprising the acetone-C5 hydrocarbon azeotrope is removed via line 46 condensed in condenser 48 and removed via line 49, with reflux being returned to the distillation column via line 45. Distillation column 42 is provided with a bottoms withdrawal line 50 and a reboiler 53. The bottoms on the azeotropic distillation contain the methyl acetate from which the acetone has been separated and this methyl acetate can be recycled to the carbonylation reaction if desired.

Appropriate reflux ratios are selected for distillation columns 13, 28 and 42 to maintain column equilibrium as is well known to persons skilled in the art. Ordinarily reflux ratios of 1:1 to 20:1 are observed.

The acetone-C5 hydrocarbon in line 49 is directed into the lower portion of extraction zone 60 and water is supplied to zone 60 through line 62. The acetone-C5 hydrocarbon azeotrope and the water flow counter-currently in zone 60 and the acetone dissolves in water and is withdrawn as an aqueous solution via line 64. The C5 hydrocarbon essentially free of acetone is withdrawn via line 66 and can be recycled to the azeotropic distillation column 28 through line 68.

The aqueous solution of acetone in line 64 can be withdrawn from the system at this point, but preferably it is separated into its components by conventional fractional distillation in distillation zone 70 in which it is introduced via line 71. Distillation zone 70 is operated at 15 to 25 psia with a temperature from 50° to 120° C. From distillation zone 70 acetone is removed as distillate via line 72, condensed in condenser 73 and withdrawn through line 75 with reflux being returned to the distillation column via line 74, a reflux ratio of 1:1 to 5:1 being employed. The bottoms stream of water, some of which passes into reboiler 77 can be withdrawn from the system via line 76 but preferably it is directed into line 78 which is connected to line 62 for recycling to extraction unit 60.

In the azeotropic distillation, sufficient C5 hydrocarbon is supplied to provide a C5 hydrocarbon to acetone ratio in zone 42 of 3:1 to 6:1. The C5 hydrocarbon is, of course, continuously recycled via lines 66 and 68. Any loss can be made up by supplying fresh C5 hydrocarbon as required. The azeotropic distillation is ordinarily carried out at 40° to 100° C. under a pressure of 20 to 40 psia.

In the water extraction zone 60 the ratio of water to C5 hydrocarbon-acetone azeotrope is 1:1 to 4:1 and the extraction can be carried out at 20° to 40° C. and under atmospheric pressure.

It will be understood that the pressure, temperature, reflux ratio and other operating values referred to above in connection with the various distillation and extraction operations are merely representative values and they may be increased or decreased as desired as will be readily apparent to persons skilled in the art.

It is believed that a fuller understanding of the invention will result from a discussion of representative carbonylation reactions with which the process of the invention will be typically associated.

Carbonylation involving an ester, such as methyl acetate, carbon monoxide and hydrogen is typically carried out at temperatures of 20° C. to 500° C., with the partial pressures of the carbon monoxide and the hydrogen each being in the range of 0.1 to 15,000 psi, and, as mentioned, the carbonylation is facilitated by the use of a catalyst, most suitably a Group VIII noble metal, i.e., rhodium, iridium, ruthenium, palladium, osmium and/or platinum, as disclosed in Belgian Pat. No. 839,320 and co-pending U.S. application Ser. No. 654,662 of Feb. 5, 1976. For ease of description, the invention will be described in terms of the carbonylation of methyl acetate. It will, of course, be understood that methyl acetate can be replaced or supplemented with dimethyl ether in the feed. It has been observed that the dimethyl ether is converted to methyl acetate in the carbonylation reaction so that it may be considered a methyl acetate precursor. When, therefore, reference is made to methyl acetate as a feed to the carbonylation, it will be understood that the dimethyl ether precursor is also contemplated.

The Group VIII noble metal carbonylation catalyst can be supplied and used in any convenient form, viz. in the zero valent state or in any higher valent form. For example, the catalyst may be the metal itself in finely-divided form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 carbon atoms. Complexes of the metals can be employed, e.g. the metal carbonyls, such as iridium and rhodium carbonyls, e.g. hexarhodium hexadecacarbonyl, or as other complexes such as the carbonyl halides, e.g. iridium tri-carbonyl chloride $[IR(CO)_3Cl]_2$ or chlorodicarbonyl rhodium dimer, or the acetylacetonates, e.g. rhodium acetylacetonate $Rh(C_5H_7O_2)_3$. It will be understood that the foregoing compounds and complexes and classes of compounds and complexes are merely illustrative of suitable forms of the Group VIII noble metal catalyst and are not intended to be limiting.

The metal employed may contain impurities normally associated with the commercially available metal or metal compounds, and need not be purified any further. Thus, the commercially available metal or metal compound is suitably employed.

The amount of Group VIII noble metal catalyst is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, the catalyst is employed in the amount of 1 mol per 10 to 100,000 mols of ester, preferably 1 mol per 50 to 10,000 mols of ester, and most preferably 1 mol per 50 to 2,000 mols of ester.

The carbon monoxide and hydrogen are preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO and $H_2$ partial pressures. The carbon monoxide and the hydrogen, like the other reactants, should, however, be essentially dry, i.e., the CO and the hydrogen and the other reactants should be reasonably free from water. The presence of minor amounts of water such as may be found in the commercial forms of the reactants is, however, acceptable.

It has been previously found that the activity of the Group VIII noble metal catalysts described above can be significantly improved, particularly with respect to reaction rate and product concentration, by the concurrent use of a promoter. Effective promoters include the elements having atomic weights greater than 5 of Groups IA, IIA, IIIA, IVB, VIB, the non-noble metals of Group VIII and the metals of the lanthanide and actinide groups of the Periodic Table. Particularly preferred are the lower atomic weight metals of each of these groups, e.g. those having atomic weights lower than 100, and especially preferred are metals of Groups IA, IIA and IIIA as are metals of the Group VIB and the non-noble metals of Group VIII. In general, the most suitable elements are lithium, magnesium, calcium, titanium, chromium, iron nickel and aluminum. The particularly preferred elements are lithium and chromium. The promoters may be used in their elemental form, e.g. as finely divided or powdered metals, or they may be employed as compounds of various types, both organic and inorganic, which are effective to introduce the element into the reaction system. Thus, typical compounds of the promoter elements include oxides, hydroxides, halides, e.g. bromides and iodides, oxyhalides, hydrides, alkoxides, and the like. Especially preferred organic compounds are the salts of organic mono-carboxylic acids, e.g. alkanoates such as acetates, butyrates, decanoates and laurates, benzoates, and the like. Other compounds include the metal alkyls, carbonyl compounds as well as chelates, association compounds and enol salts. Particularly preferred are the elemental forms, compounds which are bromides or iodides, and organic salts, e.g. salts of the mono-carboxylic acid corresponding to the anhydride being produced. Mixtures of promoters can be used, if desired, especially mixtures of elements from different Groups of the Periodic Table. The exact mechanism of the effect of the promoter, or the exact form in which the promoter acts, is not known but it has been noted that when the promoter is added in elemental form, e.g. as a finely-divided metal, a slight induction period is observed.

The quantity of promoter can vary widely but preferably it is used in the amount of 0.0001 mol to 100 mols per mol of Group VIII noble metal catalyst, most preferably 0.001 to 10 mols per mol of catalyst.

The promoter generally remains with the Group VIII metal catalyst, i.e. as one of the least volatile components, and is handled along with the catalyst.

The activity of the Group VIII noble metal catalysts described above is also significantly improved, particularly with respect to reaction rate and product concentration, catalyst stability and corrosion inhibition, by the use of an organic promoter, and particularly advantageous is the concurrent use of a promoter combination or co-promoter system containing a metal component which is a metal of Groups IVB, VB and VIB, and the non-noble metals of Group VIII, in any of the forms described above, in association or combination with an organo-nitrogen compound or an organo-phosphorus compound wherein the nitrogen and the phosphorus are trivalent.

The organic promoter can, in its broader sense, be any organo-nitrogen or organo-phosphorus compound wherein the nitrogen and phosphorus are trivalent. Preferably, however, the organo-nitrogen promoter is an amine, especially a tertiary amine of the formula

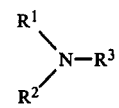

wherein $R^1$, $R^2$ and $R^3$ are the same or different and are alkyl, cycloalkyl, aryl or acyl groups which may be substituted by non-interfering groups, preferably having up to 20 carbon atoms, such as trimethylamine, triethylamine, triphenylamine, ethylenediamine tetraacetic acid, and the like, or a heterocyclic amine such as pyridine, picoline, quinoline, methylquinoline, hydroxy quinoline, pyrrole, pyrrolidine, pyrrolidone, and the like, or an imidazole, such as imidazole, methyl imidazole and the like, or an imide of a carboxylic acid which may be monobasic or polybasic and which may be aliphatic or aromatic and preferably contains up to 20 carbon atoms, such as acetic acid, succinic acid, phthalic acid, pyromellitic acid, e.g., N, N-dimethylacetamide, succinimide, phthalimide and pyromellitic diimide, or a nitrile or amide which may be aliphatic or aromatic and preferably contain up to 20 carbon atoms, e.g., acetonitrile, hexamethyl phosphoric triamide, and like imides, nitriles, and amides, or an oxime such as cyclohexanone oxime, and the like. It will be understood, however, that higher molecular weight promoters, e.g. polymeric forms of the organo-nitrogen compounds, may be used such as polyvinylpyridine, polylvinyl pyrrolidone, and the like.

The organo-phosphorus promoter is preferably a phosphine of the formula

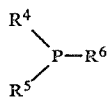

wherein $R^4$, $R^5$ and $R^6$ may be the same or different and are alkyl, cycloalkyl, aryl groups, amide groups or halogen atoms, preferably containing up to 1 to 20 carbon atoms in the case of alkyl and cycloalkyl groups and 6 to 18 carbon atoms in the case of aryl groups. Typical phosphines include trimethylphosphine, tripropylphosphine, tributyl phosphine, tricyohexylphosphine and triphenylphosphine.

Although, preferably the organic promoters are added separately to the catalyst system, it is possible to add them as complexes with the Group VIII noble metal such as the trichloro trispyridine rhodium, tris(triphenyl phosphine) rhodium, chlorotris(triphenyl phosphine) rhodium, and chlorocarbonyl bis(triphenyl phosphine) rhodium and like complexes. Both free organic promoters and complexed promoters can also be used. Indeed, when a complex of the organic promoter and the Group VIII noble metal is used, it is desirable to add free organic promoter as well. The amount of organic promoter will generally lie in the ranges referred to above for the metal promoter except that preferably up to 50 mols per mol of catalyst are employed.

The ratio of ester to the halide in the reaction system can vary over a wide range. Typically, there are used 1 to 500 equivalent of halide, preferably 1 to 200 equivalents per equivalent. Thus, there are typically used 1 to 500 mols, preferably 1 to 200 mols of ester per mol of halide reactant. By maintaining the partial pressure of carbon monoxide at the values specified, adequate amounts of the reactant are always present to react with the hydrocarbyl halide. The carbonylation step is readily carried out in a single reaction zone to which a halide source e.g., a hydrocarbyl halide such as methyl iodide, and the methyl acetate are both charged and are heated together, preferably in the liquid phase, in the presence of CO and $H_2$ and in the presence of the Group VIII metal catalyst. It will be understood that the hydrocarbyl halide may be formed in situ and the halide may thus be supplied to the system not only as the hydrocarbyl halide but the halogen moiety may also be supplied as another organic halide or as the hydrohalide or other inorganic halide, e.g. salts, such as the alkali metal or other metal salts, or even as elemental iodine or bromine.

As previously mentioned, in carrying out the carbonylation steps described above, a wide range of temperatures, e.g. 20° to 500° C. are suitable but temperatures of 80° to 350° C. are preferably employed and the more preferred temperatures generally lie in the range of 100° to 250° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under super-atmospheric pressure but excessively high pressures, which require special high-pressure equipment, are not necessary. In general, the reaction is effectively carried out by employing a carbon monoxide partial pressure which is preferably 5 to 2,000 psi, although carbon monoxide partial pressures of 0.1 to 15,000 psi can also be employed. The total pressure is that required to provide the CO and $H_2$ partial pressure and preferably that required to maintain the liquid phase. Typically, total pressures up to about 3,000 psig are used but most preferably they are at most about 1,000 psig. The reaction can be advantageously carried out in an autoclave or similar apparatus.

Molar ratios of carbon monoxide to hydrogen, broadly within the range of 1:100 to 100:1, desirably within the range of 50:1 to 1:50, and preferably within the range of 10:1 to 1:10 can be employed. Molar ratios of carbon monoxide to hydrogen within the range of 1:5 to 5:1 are especially preferred. The molar ratios of carbon monoxide to hydrogen also affect the nature of the coproducts obtained. For example, other conditions remaining constant in a liquid phase system, increasing the molar ratio of carbon monoxide to hydrogen increases the molar ratio of acetic anhydride to acetic acid produced. Conversely, reducing the molar ratio of carbon monoxide to hydrogen increases the molar ratio of acetaldehyde to acetic acid produced.

It will be apparent that the carbonylations referred to above are carried out under substantially anhydrous conditions. The presence of minor amounts of water, however, such as may be found in commercially available reactants is, as mentioned, permissible. Normally, however, the presence of more than 5 mol % of water in any one or more of the reactants should be avoided, the presence of less than 3 mol % of water desired, and the presence of less than 1 mol % is preferred.

The following example of specific application will serve to provide a fuller understanding of the invention but it will be understood that this example is given for illustrative purposes only, however, and is not to be interpreted as limitative of the invention. In the example, all parts are on a molar basis unless otherwise indicated.

EXAMPLE

Using an apparatus system such as illustrated in the drawing, a mixture composed of 80 mol % methyl acetate, 8 mol % methyl iodide, 2 mol % palladium acetate and 10 mol % of tributyl phosphine is charged to a stirred pressure reactor 10. This mixture is heated to 160° C. and a 53:47 percent by volume mixture of carbon monoxide and hydrogen, respectively, is introduced into the reactor to provide and maintain a total pressure of 650 psig. Continuous liquid feed to the reactor is then begun. The conditions of temperature and pressure in the reactor are such that a large proportion of the reaction mixture is vaporized in the course of the reaction. These vaporized volatile components are continuously withdrawn and treated as will be described below to separate the various components and to recycle to the reactor methyl acetate, methyl iodide and some acetone. The reaction is carried out to provide a residence time in the reactor of about 2 hours. Thus, during continuous operation, while maintaining the above-noted pressure of carbon monoxide and hydrogen, there are continuously fed to the reactor approximately 4300 parts per hour of methyl acetate (including 3000 parts per hour of recycle methyl acetate) and 585 parts per hour of recycle methyl iodide, and 75 parts per hour of recycle acetone. The vaporized volatile components are continuously withdrawn as a vaporous effluent, condensed to separate non-condensible gases present, which are recycled to the reactor, these gases being purged as necessary to remove by-products such as methane, and compressed to the reactor pressure and the liquid condensate is then fractionally distilled at a temperature of 40° to 120° C. under a pressure of 30 psig to separate acetaldehyde. The remainder of the condensed effluent which is then fed to the process of this invention comprises a mixture of 585 parts per hour of methyl iodide, 3055 parts per hour of methyl acetate, 115 parts per hour of acetone and 1370 parts per hour of the heavier components, acetic anhydride, ethylidene diacetate, acetic acid and vinyl acetate.

This feed is supplied to fractional distillation column 13 which is operated at a temperature of 40° to 90° C. and under a pressure of 5 psig and with a reflux ratio of 15:1. The distillate from this distillation comprises all of the methyl iodide, 75 parts per hour of acetone and 62 parts per hour of methyl acetate. This distillate is recycled to the reactor. The bottoms from this distillation are then passed to fractional distillation column 28 wherein the acetone and the methyl acetate are separated as distillate from the remainder of the feed to this column which is operated at a temperature of 40° to 140° C. and under a pressure of 3 psig, with a reflux ratio of 3. This distillate is then fed to azeotropic distillation column 42 which is also fed with 250 parts per hour of pentane to provide a pentane to acetone ratio of about 4:1. Column 42 is operated with a temperature of 40° to 100° C., a pressure of 30 psi and with a reflux ratio of 18:1. As a result of the azeotropic distillation which takes place in column 42, an acetone-pentane azeotrope is removed as distillate and the approximately 3,000 parts per hour of methyl acetate in the feed are removed as bottoms product and recycled to reactor 10.

The acetone-pentane azeotropic mixture is then fed at the rate of about 310 parts per hour to extraction column 60 where it is brought into counter-current contact with water at a temperature of about 30° C. introduced at the rate of about 500 parts per hour. The insoluble pentane is recycled to azeotropic distillation column 45 and the aqueous solution of acetone is then fractionally distilled in fractional distillation column 70 operated at a temperature of 60° to 120° C., a pressure of 5 psig and a reflux ratio of 3:1. The acetone is removed as distillate and withdrawn from the system and the water, obtained as the bottoms of this distillation is recycled to the extraction column 60.

In this way, the net "make" of acetone in the reactor is effectively separated, using recycling excess acetone which maintains a molar ratio of acetone to methyl iodide always at least 1 to 10, preferably at least 1.5 to 10.

What is claimed is:

1. A process for the recovery of acetone from the volatile components of the carbonylation reaction mixture produced during the reaction in a carbonylation zone of methyl acetate with carbon monoxide in the presence of a Group VIII noble metal and in the presence of methyl iodide which comprises establishing an acetone to methyl iodide molar ratio of at least 1:10 in the volatile component mixture by supplying acetone, methyl iodide and methyl acetate to the carbonylation zone, fractionally distilling said volatile component mixture to separate as distillate essentially all of said methyl iodide and some of said acetone and methyl acetate, the amount of acetone separated substantially corresponding to the amount supplied to the reaction, distilling the remaining acetone and methyl acetate from the bottoms of said distillation and therefore treating the methyl acetate-acetone mixture to recover acetone therefrom, and recycling to the carbonylation zone the methyl acetate remaining after recovery of acetone from the methyl acetate-acetone mixture.

2. A process as defined in claim 1, wherein the supplied acetone is provided by recycling said distillate to the carbonylation zone.

3. A process as defined in claim 1, wherein the acetone is recovered from the methyl acetate-acetone mixture by azeotropic distillation.

4. A process as defined in claim 1, wherein the acetone to methyl iodide molar ratio is at least 1.5:10.

* * * * *